US009618465B2

United States Patent
Kocanda et al.

(10) Patent No.: US 9,618,465 B2
(45) Date of Patent: Apr. 11, 2017

(54) HYDROGEN SENSOR

(71) Applicants: Martin Kocanda, Streamwood, IL (US); Michael James Haji-Sheikh, DeKalb, IL (US)

(72) Inventors: Martin Kocanda, Streamwood, IL (US); Michael James Haji-Sheikh, DeKalb, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 163 days.

(21) Appl. No.: 14/247,036

(22) Filed: Apr. 7, 2014

(65) Prior Publication Data

US 2014/0326615 A1 Nov. 6, 2014

Related U.S. Application Data

(60) Provisional application No. 61/818,110, filed on May 1, 2013.

(51) Int. Cl.
*G01N 27/02* (2006.01)
*G01N 33/00* (2006.01)

(52) U.S. Cl.
CPC .......... *G01N 27/02* (2013.01); *G01N 33/005* (2013.01)

(58) Field of Classification Search
CPC .......... G01N 27/02; G01N 7/00; G01N 33/20; G01N 31/10; H01G 13/00; H01L 21/34; H01M 8/042; H01M 8/02
See application file for complete search history.

(56) References Cited

U.S. PATENT DOCUMENTS

| 4,058,368 | A | | 11/1977 | Svensson et al. |
| 5,716,506 | A | * | 2/1998 | Maclay .............. G01N 27/4045 204/424 |
| 6,231,744 | B1 | | 5/2001 | Ying et al. |
| 7,001,669 | B2 | | 2/2006 | Lu et al. |
| 7,171,841 | B2 | | 2/2007 | Xu et al. |
| 7,179,561 | B2 | | 2/2007 | Niu et al. |
| 7,186,381 | B2 | | 3/2007 | Penner et al. |
| 8,187,865 | B2 | | 5/2012 | Yun et al. |
| 8,839,659 | B2 | | 9/2014 | Xiao |
| 2003/0008505 | A1 | | 1/2003 | Chen et al. |
| 2003/0072885 | A1 | | 4/2003 | Lee et al. |
| 2004/0106203 | A1 | | 6/2004 | Stasiak et al. |
| 2004/0118698 | A1 | | 6/2004 | Lu et al. |

(Continued)

FOREIGN PATENT DOCUMENTS

| EP | 1 426 756 | 6/2004 |
| EP | 2 362 216 | 8/2011 |

(Continued)

OTHER PUBLICATIONS

Jelley (IEEE, vol. ED-24, No. 10, 1987).*

(Continued)

*Primary Examiner* — Jennifer Dieterle
(74) *Attorney, Agent, or Firm* — Evan Law Group LLC

(57) ABSTRACT

A capacitor for a hydrogen sensor includes a dielectric substrate, a first electrode on the dielectric substrate, a second electrode on the dielectric substrate, and palladium islands on the dielectric substrate and between the first and second electrodes. The palladium islands are electrically isolated from the first and second electrodes and from each other.

20 Claims, 6 Drawing Sheets

(56) References Cited

U.S. PATENT DOCUMENTS

| | | | |
|---|---|---|---|
| 2004/0146735 | A1 | 7/2004 | Weiner et al. |
| 2005/0247961 | A1 | 11/2005 | Zhou |
| 2005/0258051 | A1* | 11/2005 | Ono .................... G01N 27/125 205/775 |
| 2006/0046480 | A1 | 3/2006 | Guo |
| 2006/0131695 | A1 | 6/2006 | Kuekes et al. |
| 2006/0263255 | A1 | 11/2006 | Han et al. |
| 2006/0289351 | A1 | 12/2006 | Xiao et al. |
| 2007/0040191 | A1 | 2/2007 | Bezryadin et al. |
| 2007/0077429 | A1 | 4/2007 | Mirkin et al. |
| 2007/0087470 | A1 | 4/2007 | Sunkara et al. |
| 2007/0209576 | A1 | 9/2007 | Sunkara et al. |
| 2008/0078234 | A1 | 4/2008 | Monty et al. |
| 2008/0206555 | A1 | 8/2008 | Choi et al. |
| 2009/0017363 | A1 | 1/2009 | Niu et al. |
| 2009/0035525 | A1 | 2/2009 | Garcia et al. |
| 2009/0084159 | A1 | 4/2009 | Sun et al. |
| 2009/0233086 | A1 | 9/2009 | Hirai |
| 2009/0302857 | A1* | 12/2009 | Harada ................ G01N 33/005 324/444 |
| 2010/0005853 | A1* | 1/2010 | Visel et al. ................... 73/19.07 |
| 2010/0200199 | A1 | 8/2010 | Habib et al. |
| 2010/0212403 | A1* | 8/2010 | Seal ..................... G01N 33/005 73/31.06 |
| 2010/0269569 | A1 | 10/2010 | Yang et al. |
| 2011/0053020 | A1 | 3/2011 | Norton et al. |
| 2011/0189510 | A1 | 8/2011 | Caracciolo et al. |
| 2011/0259083 | A1* | 10/2011 | Lee ..................... G01N 27/127 73/31.05 |
| 2011/0274882 | A1 | 11/2011 | Wallace et al. |
| 2011/0275005 | A1 | 11/2011 | Zhu et al. |
| 2012/0034410 | A1 | 2/2012 | Baumgart et al. |
| 2012/0036919 | A1 | 2/2012 | Kamins et al. |
| 2012/0094192 | A1 | 4/2012 | Qu et al. |
| 2012/0134880 | A1 | 5/2012 | Kurkina et al. |
| 2012/0147587 | A1 | 6/2012 | Wober |
| 2012/0282540 | A1 | 11/2012 | Niu et al. |
| 2015/0121992 | A1 | 5/2015 | Xiao |

FOREIGN PATENT DOCUMENTS

| | | |
|---|---|---|
| KR | 20090007443 | 1/2009 |
| KR | 100959245 | 5/2010 |
| WO | 2008/153593 | 12/2008 |
| WO | 2012/047869 | 4/2012 |

OTHER PUBLICATIONS

Lee, K-B. et al., "Size-controlled synthesis of Pd nanowires using a mesoporous silica template via chemical vapor infiltration", Advanced Materials, vol. 13, No. 7, pp. 517-520, (2001).

Huang, M.H. et al., "Ag nanowire formation within mesoporous silica", Chemical Communication, pp. 1063-1064, (2000).

Applicant's remarks in U.S. Appl. No. 13/245,674, pp. 5-10, dated Mar. 25, 2014.

Singh, S.K., "Industrial Instrumentation and Control", Tata McGraw-Hill, Third Edition, pp. 140-145, (2008).

Kiang, C-H. et al., "Molecular nanowires of 1 nm diameter from capillary filling of single-walled carbon nanotubes", The Journal of Physical Chemistry B, vol. 103, pp. 7449-7551, (1999).

U.S. Appl. No. 14/482,581 mailed on Feb. 23, 2016, 10 pages.

Invitation to Pay Additional Fees with Partial International Search Report dated Jan. 27, 2012 for PCT application No. PCT/US2011/054742.

WO Application No. PCT/US2011/054742, mailed Jan. 27, 2012, 5 pages.

WO Application No. PCT/US2011/054742, mailed Apr. 2, 2012, 16 pages.

WO Application No. PCT/US2011/054742, mailed Apr. 18, 2013, 11 pages.

U.S. Appl. No. 13/245,674, mailed Apr. 11, 2013, 14 pages.

U.S. Appl. No. 13/245,674, mailed Oct. 1, 2013, 13 pages.

U.S. Appl. No. 13/245,674, mailed Jul. 16, 2014, 9 pages.

U.S. Appl. No. 13/245,674, filed Sep. 26, 2011.

Ramanathan, M. et al., "Crossover behavior in the hydrogen sensing mechanism for palladium ultrathin films", Nanotechnology, vol. 21, pp. 125501-1-125501-6, (2010).

U.S. Department of Energy, "Fuel cell technologies program multi-year research, development and demonstration plan", found at www1.eere.energy.gov/hydrogenandfuelcells/mypp/index.html, printed on Feb. 15, 2012.

Tabib-Azar, M. et al., "Highly sensitive hydrogen sensors using palladium coated fiber optics with exposed cores and evanescent field interactions", SPIE, Microelectronic Structures and MEMS for Optical Processing IV, proceedings vol. 3513, pp. 80-88, (1998).

Crabtree, G.W. "The hydrogen economy", Physics Today, vol. 57, pp. 39-44, (2004).

Jardine, A.P. "Hydrogen sensors for hydrogen fuel cell applications", Darnell Group, pp. 1-4, found at www.powerpulse.net/techPaper.php?paperID=99, printed on Feb. 14, 2012.

Buttner, W.J. et al., "An overview of hydrogen safety sensors and requirements", International Journal of Hydrogen Energy, vol. 36, pp. 2462-2470, (2011).

Kong, J. et al., "Functionalized carbon nanotubes for molecular hydrogen sensors", Advanced Materials, vol. 13, No. 18, pp. 1384-1386, (2001).

Favier, F. et al., "Hydrogen sensors and switches from electrodeposited palladium mesowire arrays", Science, vol. 293, issue 5538, pp. 2227-2231, (2001).

Walter, E.C. et al., "Palladium mesowire arrays for fast hydrogen sensors and hydrogen-actuated switches", Analytical Chemistry, vol. 74, No. 7, pp. 15461553, (2002).

Tibuzzi, A. et al., "Polysilicon mesoscopic wires coated by Pd as high sensitivity H2 sensors", Sensors and Actuators B, vol. 83, pp. 175-180, (2002).

Varghese, O.K. et al., "Extreme changes in the electrical resistance of titania nanotubes with hydrogen exposure", Advanced Materials, vol. 15, No. 7-8, pp. 624-627, (2003).

Varghese, O.K. et al., "Hydrogen sensing using titania nanotubes", Sensors and Actuators B, vol. 93, pp. 338-344, (2003).

Xu, T. et al., "Self-assembled monolayer-enhanced hydrogen sensing with ultrathin palladium films", Applied Physics Letters, vol. 86, pp. 203104-1-203104-3, (2005).

Paulose, M. et al., "Unprecedented ultra-high hydrogen gas sensitivity in undoped titania nanotubes", Nanotechnology, vol. 17, pp. 398-402, (2006).

Ding, D. et al., "Volume-expansion-enhanced pinning of nanoporous Pd films for detection of high-concentration hydrogen", Sensor Letters, vol. 4, pp. 331-333, (2006).

Ding, D. et al., "A pyrolytic, carbon-stabilized, nanoporous Pd film for wide-range $H_2$ sensing", Advanced Materials, vol. 19, pp. 1996-1999, (2007).

Khanuja, M. et al., "Pulse like hydrogen sensing response in Pd nanoparticle layers", Applied Physics Letters, vol. 91, pp. 253121-1-253121-3, (2007).

van Lith, J. et al., "A hydrogen sensor based on tunneling between palladium clusters", Applied Physics Letters, vol. 91, pp. 181910-1-181910-3, (2007).

Sun, Y. et al., "High-performance, flexible hydrogen sensors that use carbon nanotubes decorated with palladium nanoparticles", Advanced Materials, vol. 19, pp. 2818-2823, (2007).

Kiefer, T. et al., "A single nanotrench in a palladium microwire for hydrogen detection", Nanotechnology, vol. 19, pp. 125502-1-125502-9, (2008).

Joshi, R.K. et al., "Pd nanoparticles and thin films for room temperature hydrogen sensor" Nanoscale Research Letters, vol. 4, pp. 1191-1196, (2009).

Yang, F. et al., "Fast, sensitive hydrogen gas detection using single palladium nanowires that resist fracture", Nano Letters, vol. 9, No. 5, pp. 2177-2182, (2009).

Jeon, K.J. et al., "Finite size effect on hydrogen gas sensing performance in single Pd nanowires", Nanotechnology, vol. 19, pp. 495501-1-495501-6, (2008).

(56) References Cited

OTHER PUBLICATIONS

Offermans, P. et al., "Ultralow-power hydrogen sensing with single palladium nanowires", Applied Physics Letters, vol. 94, pp. 223110-1-223110-3, (2009).
Khanuja, M. et al., "Concentration-specific hydrogen sensing behavior in monosized Pd nanoparticle layers", Nanotechnology, vol. 20, pp. 015502-1-015502-7, (2009).
Yang, F. et al., "Joule heating a palladium nanowire sensor for accelerated response and recovery to hydrogen gas", Small, vol. 6, No. 13, pp. 1422-1429, (2010).
Yang, F. et al., "Smaller is faster and more sensitive: the effect of wire size on the detection of hydrogen by single palladium nanowires", ACS Nano, vol. 4, No. 9, pp. 5233-5244, (2010).
Agar, P. et al., "Sensing response of palladium nanoparticles and thin films to deuterium and hydrogen: Effect of gas atom diffusivity", Sensors and Actuators B: Chemical, vol. 150, pp. 686-691, (2010).
Kiefer, T. et al., "The transition in hydrogen sensing behavior in noncontinuous palladium films", Applied Physics Letters, vol. 97, pp. 121911-1-121911-3, (2010).
Kiefer, T. et al., "Fast and robust hydrogen sensors based on discontinuous palladium films on polyimide, fabricated on a wafer scale", Nanotechnology, vol. 21, pp. 505501-1-505501-5, (2010).
Zou, J. et al., "Hydrogen-induced reversible insulator-metal transition in a palladium nanosphere sensor", Small, vol. 6, No. 21, pp. 2358-2361, (2010).
Lu, C. et al., "MOS hydrogen sensor with very fast response based on ultra-thin thermal $SiO_2$ film", International Journal of Hydrogen Energy, vol. 35, pp. 12561-12567, (2010).
Sekhar, P.K. et al., "Development and testing of a miniaturized hydrogen safety sensor prototype", Sensors and Actuators B: Chemical, vol. 148, pp. 469-477, (2010).
Lee, J.M. et al., "Effects of surface roughness on hydrogen gas sensing properties of single Pd nanowires", Journal of Nanoscience and Nanotechnology, vol. 11, pp. 2151-2154, (2011).
Kim, K.R. et al., "Suppression of phase transitions in Pd thin films by insertion of a Ti buffer layer", Journal of Material Science, vol. 46, pp. 1597-1601, (2011).
Noh, J-S. et al., "Low-dimensional palladium nanostructures for fast and reliable hydrogen gas detection", Sensors, vol. 11, pp. 825-851, (2011).
Zeng, X.Q. et al., "Hydrogen gas sensing with networks of ultrasmall palladium nanowires formed on filtration membranes", Nano Letters, vol. 11, pp. 262-268, (2011).
Knight, B. et al., "Development of sensors for automotive PEM-based fuel cells", United Technologies Corporation, Fuel Cells Division, 243 pages, found at www.lanl.gov/orgs/mpa/mpa11/FinalReportforDOESensorsContractUTRC.pdf, (2005).
Liu, R-J. et al., "In situ electron microscopy studies of the sintering of palladium nanoparticles on alumina during catalyst regeneration processes", Microscopy and Microanalysis, vol. 10, pp. 77-85, (2004).
Baker, R.T.K. et al., "The interaction of palladium with alumina and titanium-oxide supports", Journal of Catalysis, vol. 89, pp. 422-432, (1984).
Xiao, Z.L. et al., "Fabrication of alumina nanotubes and nanowires by etching porous alumina membranes", Nano Letters, vol. 2, No. 11, pp. 1293-1297, (2002).
Crispin R.M. et al., "The wetting and bonding behaviour of some nickel alloy-alumina systems", Journal of Materials Science, vol. 11, pp. 17-21, (1976).
Asthana, R. et al., "Wettability and interface considerations in advanced heat-resistant Ni-base composites", Bulletin of the Polish Academy of Sciences, Technical Sciences, vol. 54, No. 2, pp. 147-166, (2006).
Welp, U. et al., "Superconducting transition and vortex pinning in Nb films patterned with nano-scale hole-arrays", Physical Review B., vol. 66, pp. 212507-1-212507-17, (2002).
Xiao, Z.L. et al., "Nickel antidot arrays on alumina substrates", Applied Physics Letters, vol. 81, No. 15, pp. 2869-2871, (2002).
Kulkarni, A.K. et al., "Electrical and structural characteristics of chromium thin films deposited on glass and alumina substrates", Thin Solid Films, vol. 301, pp. 17-22, (1997).
Matula, R.A. "Electrical resistivity of copper, gold, palladium, and silver", Journal of Physical Chemistry Reference Data, vol. 8, No. 4, pp. 1147-1298, (1979).
Ealet, B. et al., "A surface analytical study of the formation and adhesion of chromium films on alumina", Journal of Adhesion Science and Technology, vol. 6, No. 11, pp. 1221-1231, (1992).
Sakamoto, Y. et al., "Electrical resistance measurements as a function of composition of palladium-hydrogen (deuterium) systems by a gas phase method", Journal of Physics: Condensed Matter, vol. 8, pp. 3399-3411, (1996).
Thomas, R.C. et al., "Sensors for detecting molecular hydrogen based on Pd metal alloys", Journal of the Electrochemical Society, vol. 144, No. 9, pp. 3245-3249, (1997).
Suleiman, M. et al., "Phase transition and lattice expansion during hydrogen loading of nanometer sized palladium clusters", Journal of Alloys and Compounds, vol. 356-357, pp. 644-648, (2003).
Sachs, C. et al., "Solubility of hydrogen in single-sized palladium clusters", Physical Review B, vol. 64, pp. 075408-1-075408-10, (2001).
Di Vece, M. et al., "Hydrogen-induced ostwald ripening at room temperature in a Pd nanocluster film", Physical Review Letters, vol. 100, pp. 236105-1-236105-4, (2008).
Liekhus, K.J. et al., "Flammability of gas mixtures containing volatile organic compounds and hydrogen", Journal of Loss Prevention in the Process Industries, vol. 13, issues 3-5, pp. 377-384, (2000).
"Hydrogen Leak Detector for Vehicle Fuel Cell Applications", pp. 1-3, found at www.fuelcellsensor.com, printed on Feb. 15, 2012.
Bodzenta, J. et al., "Thin palladium film as a sensor of hydrogen gas dissolved in transformer oil", Sensors and Actuators B, vol. 87, pp. 82-87, (2002).
Christofides, C. et al., "Solid-state sensors for trace hydrogen gas detection", Journal of Applied Physics, vol. 68, No. 6, pp. R1-R30, (1990).
Chen, H-I. et al., "A novel high-sensitive Pd/InP hydrogen sensor fabricated by electroless plating", Sensors and Actuators B, vol. 85, pp. 10-18, (2002).
Wang, C. et al., "Detectivity comparison between thin-film Pd/PVDF photopyroelectric interferometric and optical reflectance hydrogen sensors", Review of Scientific Instruments, vol. 70, No. 11, pp. 4370-4376, (1999).
Sutapun, B. et al., "Pd-coated elastooptic fiber optic Bragg grating sensors for multiplexed hydrogen sensing", Sensors and Actuators B, vol. 60, pp. 27-34, (1999).
Pundt, A. "Hydrogen in nano-sized metals", Advanced Engineering Materials, vol. 6, No. 1-2, pp. 11-21, (2004).
Lee, E. et al., "Hysteresis behavior of electrical resistance in Pd thin films during the process of absorption and desorption of hydrogen gas", International Journal of Hydrogen Energy, vol. 35, pp. 6984-6991, (2010).
Jeon, K.J. et al., "Individual Pd nanowire hydrogen sensors fabricated by electron-beam lithography", Nanotechnology, vol. 20, pp. 135502-1-135502-5, (2009).
Yu, S. et al., "Fabrication of palladium nanotubes and their application in hydrogen sensing", Chem. Mater., vol. 17, No. 13, pp. 3445-3450, (2005).
Menke, E.J. et al., "Lithographically patterned nanowire electrodeposition", Nature Materials, vol. 5, pp. 914-919, (2006).
"The Anopore inorganic membrane", found at www.whatman.com/PRODAnoporeInorganicMembranes.aspx., 3 pages, (2009).
Narehood, D.G. et al., "X-ray diffraction and H-storage in ultra-small palladium particles", International Journal of Hydrogen Energy, vol. 34, pp. 952-960, (2009).
Eastman, J.A. et al., "Narrowing of the palladium-hydrogen miscibility gap in nanocrystalline palladium", Physical Review B, vol. 48, No. 1, pp. 84-93, (1993).
Hughes, R.C. et al., "Thin films of Pd/Ni alloys for detection of high hydrogen concentrations", Journal of Applied Physics, vol. 71, No. 1, pp. 542-544, (1992).

(56) References Cited

OTHER PUBLICATIONS

Ding, D. et al., "Hydrogen sensing of nanoporous palladium films supported by anodic aluminum oxides", Sensors and Actuators B, vol. 120, pp. 182-186, (2006).

Hakamada, M. et al., "Hydrogen storage properties of nanoporous palladium fabricated by dealloying", Journal of Physical Chemistry C, vol. 114, pp. 868-873, (2010).

NIU Media Relations & Internal Communications, "NIU scientists find fast, easy way to make hydrogen nanosensors", found at www.niu.edu/mediarelations/news/2011/01/hydrogen_nano.shtml, 1 page, Jan. 12, 2011.

Zeng, X.-Q. et al., "Networks of ultrasmall Pd/Cr nanowires as high performance hydrogen sensors", ACS Nano, vol. 5, No. 9, pp. 7443-7452, (2011).

Kim, K.T. et al., "Hydrogen gas sensor using pd nanowires electrodeposited into anodized alumina template", IEEE Sensors Journal, vol. 6, No. 3, pp. 509-513, (2006).

Lin, C. et al., "Hydrogen spillover enhanced hydriding kinetics of palladium-doped lithium nitride to lithium imide", The Journal of Physical Chemistry C, vol. 113, No. 19, pp. 8513-8517, (2009).

International Search Report dated Apr. 2, 2012 for PCT application No. PCT/US2011/054742.

Lin, C. et al., "An in situ electrical study on primary hydrogen spillover from nanocatalysts to amorphous carbon support", Applied Physics Letters, vol. 93, pp. 233110-1-233110-3, (2008).

Srinivasan, U. et al., "Alkyltrichlorosilane-based self-assembled monolayer films for stiction reduction in silicon micromachines", Journal of Microelectromechanical Systems, vol. 7, issue 2, pp. 252-260, (1998).

Zeng, X.Q. et al., "Hydrogen responses of ultrathin Pd films and nanowire networks with a Ti buffer layer", Journal of Materials Science, vol. 47, pp. 6447-6651, (2012).

Ali, M., et al. "Pt/GaN Schottky diodes for hydrogen gas sensors", Sensors and Actuators B: Chemical, vol. 113, No. 2, pp. 797-804, (2006).

Neudeck, P.G. et al., "Hydrogen gas sensors fabricated on atomically flat 4H-SiC webbed cantilevers", Materials Science Forum, vol. 600-603, pp. 1199-1202, (2009).

Kocanda, M. et al., "Detection of cyclic volatile organic compounds using single-step anodized nanoporous alumina sensors", IEEE Sensors Journal, vol. 9, No. 7, pp. 836-841, (2009).

Kocanda, M. et al., "Enhanced hydrogen sensing employing electrodeposited palladium nanowires enclosed in anodized aluminum oxide nanopores", IEEE Sensors Conference, pp. 308-311, (2009).

Syaifudin, A.R.M. et al., "Measurements and performance evaluation of novel interdigital sensors for different chemicals related to food poisoning", IEEE Sensors Journal, vol. 11, No. 11, pp. 2957-2965, (2011).

Syaifudin, A.R.M. et al., "Modelling and fabrication of optimum structure of novel interdigital sensors for food inspection", International Journal of Numerical Modelling: Electronic Networks, Devices and Fields, vol. 25, issue 1, pp. 64-81, (2012).

Syaifudin, A.R.M. et al., "A low cost novel sensing system for detection of dangerous marine biotoxins in seafood", Sensors and Actuators B: Chemical, vol. 137, issue 1, pp. 67-75, (2009).

Wang, D. et al., "Development of ultra-high density silicon nanowire arrays for electronics applications", Nano Research, vol. 1, pp. 9-21, (2008).

Ebrahimi, N. et al., "Reliability of sensors based on nanowire networks", IIE Transactions, vol. 45, No. 2, pp. 215-228, (2013).

Du, Y. et al., "SERS enhancement dependence on the diameter and aspect ratio of silver-nanowire array fabricated by anodic aluminum oxide template", Applied Surface Science, vol. 255, pp. 1901-1905, (2008).

Kumar, M.K. et al., "Palladium dispersed multiwalled carbon nanotube based hydrogen sensor for fuel cell applications", International Journal of Hydrogen Energy, vol. 32, issue 13, pp. 2518-2526, (2007).

Pavlovsky, I. et al., "Palladium nanoparticles hydrogen sensor", Sensors & Transducers Journal, vol. 73, issue 11, pp. 793-798, (2006).

Mubeen, S. et al., "Palladium nanoparticles decorated single-walled carbon nanotube hydrogen sensor", Journal of Physical Chemistry C, vol. 111, No. 17, pp. 6321-6327, (2007).

Product description for "MNPS-B Hydrogen Sensor", Applied Nanotech, Inc., 3 pages, (2009).

U.S. Appl. No. 14/482,581 mailed Jul. 8, 2015, 20 pages.

U.S. Appl. No. 14/482,581, filed Sep. 10, 2014.

* cited by examiner

HYDROGEN SENSOR

BACKGROUND

Hydrogen ($H_2$) gas is highly volatile and, when in contact with oxygen, can become extremely flammable and highly explosive. The use of effective hydrogen sensors to accurately and quickly respond to hydrogen gas leaks and to monitor manufacturing and distribution will be crucial for the safe deployment of all hydrogen-based applications. Hydrogen sensors must be sensitive enough to discriminate between ambient low-level traces of hydrogen and those that are generated by a hydrogen leak.

Palladium based hydrogen sensors have a unique advantage in that the surface of palladium can act catalytically to break the H—H bond in diatomic hydrogen, allowing monatomic hydrogen to diffuse into the material. Furthermore, palladium can dissolve more than 600 times its own volume of hydrogen, but dissolves little of the other common gases such as nitrogen, oxygen, nitrogen monoxide, carbon dioxide, and carbon monoxide. This allows palladium to be the most selective hydrogen sensing material. Finally, the palladium hydrogenation process is reversible at room temperature, enabling simpler designs.

In the presence of hydrogen the resistance of palladium will change due to the formation of a solid solution of (at low $H_2$ pressure, α-phase) or a hydride (at high $H_2$ pressure, β-phase). The level of dissolved hydrogen changes the electrical resistivity of the metal and also its volume due to the formation of metal hydride. Consequently, conventional hydrogen sensors have been fabricated from bulk materials, by applying palladium metal to bulk substrates. Recent developments in semiconductor processes have also allowed the detection and measurement of hydrogen using Schottky junctions including palladium; in this case, the metal-semiconductor junctions are affected by the diffusion of hydrogen. All these sensors use a change in resistivity of the palladium caused by the change in crystal structure to detect hydrogen, measured by injection of current.

Typically, technology which relies upon the resistive response of hydrogen diffusion into palladium cannot measure hydrogen concentrations above 4% (volume/volume; the threshold of hydrogen in air which can cause an explosion). Furthermore, failure of the sensors occurs upon exposure of the device to hydrogen concentration greater than 5% (volume/volume). The major failure modes of the sensors seem to be some form of stiction (static friction), caused by the injection of direct current through the bulk material, thus altering the crystal structure.

SUMMARY

In a first aspect, the present invention is a capacitor for a hydrogen sensor, comprising a dielectric substrate, a first electrode, on the dielectric substrate, a second electrode, on the dielectric substrate, and palladium islands, on the dielectric substrate and between the first and second electrodes. The palladium islands are electrically isolated from the first and second electrodes and from each other.

In a second aspect, the present invention is a hydrogen sensor, comprising the capacitor for a hydrogen sensor, and electrical leads, on the substrate, electrically connected to the first and second electrodes.

In a third aspect, the present invention is a device for detecting hydrogen, comprising the hydrogen sensor, and means for measuring impedance, electrically connected to the hydrogen sensor.

In a fourth aspect, the present invention is a method of measuring concentration of hydrogen gas, comprising exposing the capacitor to hydrogen gas; and measuring the impedance of the capacitor.

In a fifth aspect, the present invention is a method of forming a capacitor for hydrogen sensing, comprising forming first and second electrodes on a dielectric substrate; and forming palladium islands, on the substrate, between the first and second electrodes.

DETAILED DESCRIPTION

The present invention makes use of the discovery of a hydrogen sensor containing palladium islands, which are electrically isolated. The sensor includes a capacitor having a dielectric region which includes the palladium islands. The sensor determines the concentration of hydrogen to which it is exposed based on the impedance of the capacitor. As hydrogen diffuses into the palladium islands, the dielectric value of the dielectric region changes, causing a change in impedance.

Figure 1:
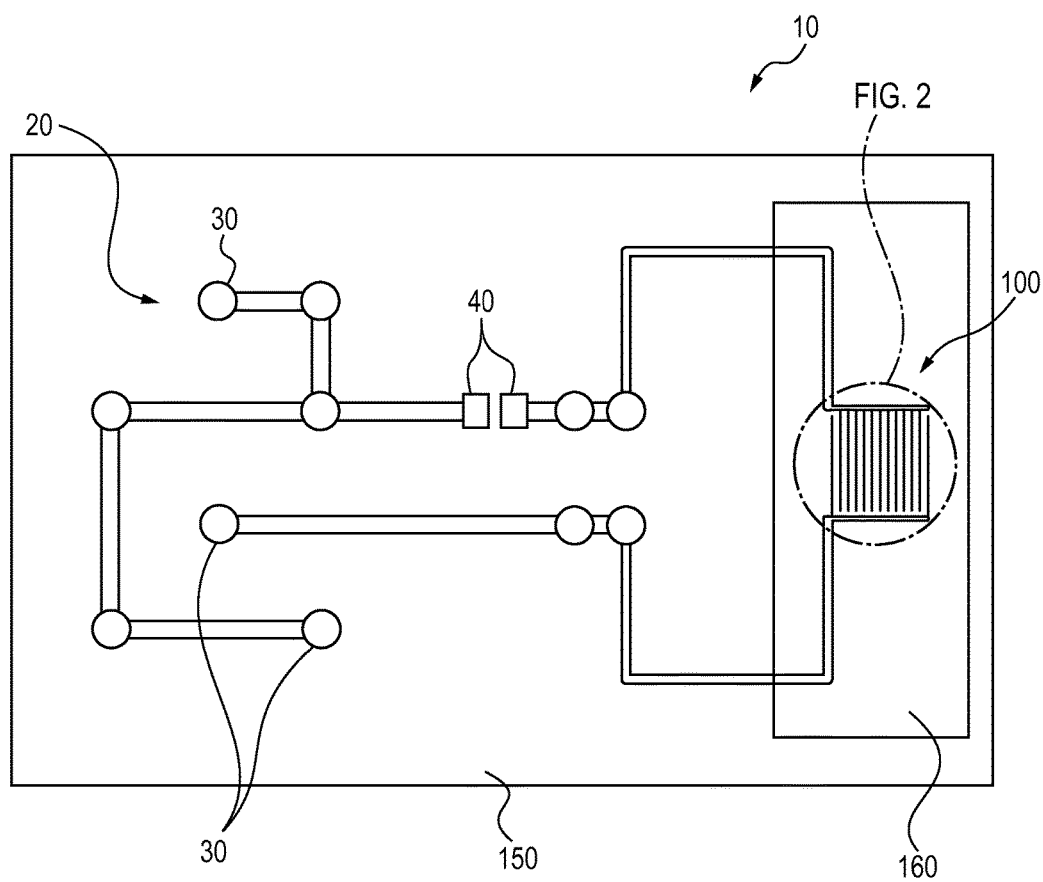
FIG. 1 illustrates a hydrogen sensor.

A sensor is illustrated in FIG. 1. The sensor, 10, includes a capacitor, 100, on a dielectric substrate, 150, and palladium islands, 160, on the dielectric substrate. Also illustrated are leads, 20, electrically connected to the sensor. The leads include connection leads, 30, for electrically connecting the sensor for measurement of impedance of the capacitor for the measurement of the hydrogen concentration, and optional pad, 40, for connection of a resistor or short.

Figure 2:
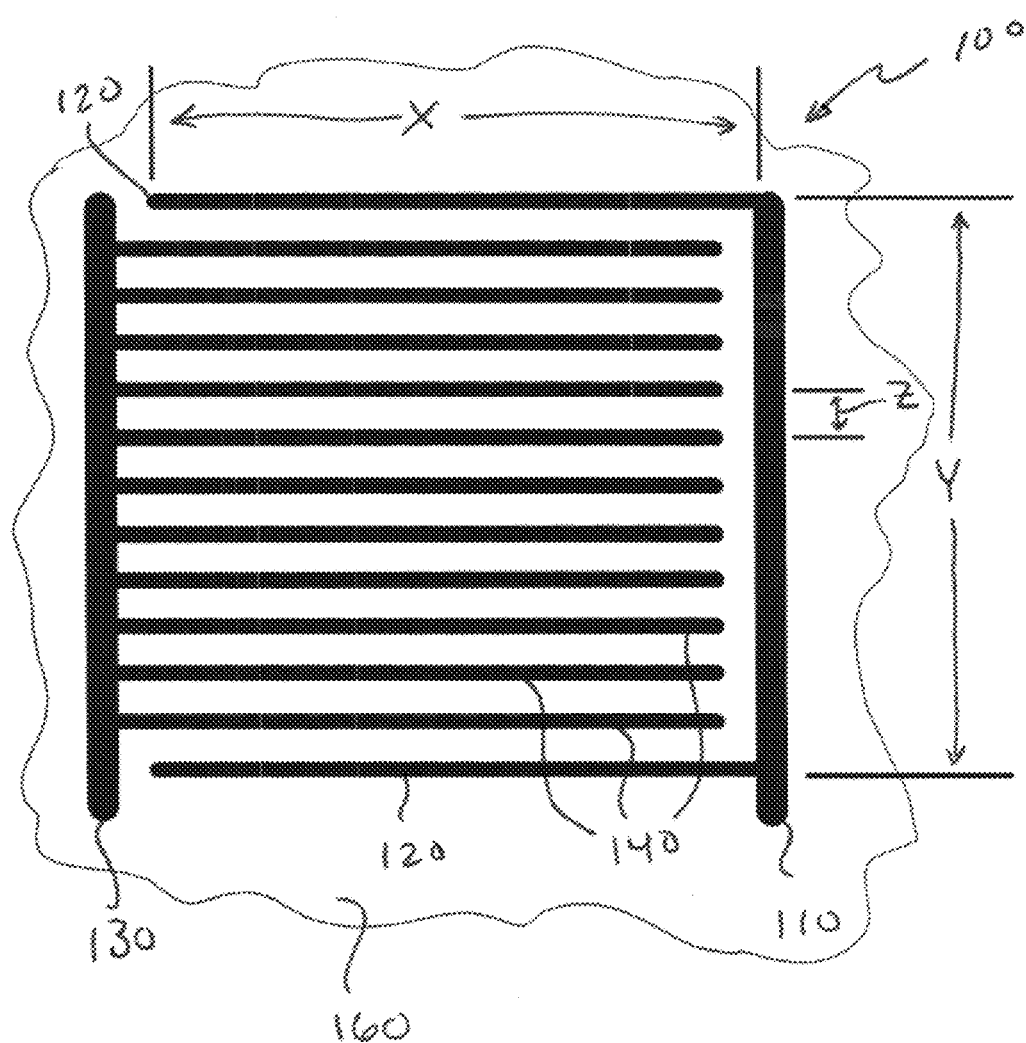
FIG. 2 illustrates capacitor geometry of a hydrogen sensor.

Details of the capacitor, 100, are shown in FIG. 2. The capacitor includes first electrode, 110, and second electrode, 130. The capacitor also includes palladium islands, 160, on the dielectric substrate (not illustrated) between the first and second electrodes. Also illustrated are optional subelectrode of the positive and negative electrodes, 120 and 140, respectively. The distance X represents the width of the capacitor, the distance Y represents the length of the capacitor, and the distance Z represents the interdigitated subelectrode distance or pitch. The first and second electrodes and their subelectrodes may be referred to as "positive" and "negative", however, since impedance is measure using an alternating current (AC), such designations are arbitrary.

The dielectric region of the capacitor includes those regions through which the electric field created by the charge on the capacitor passes; this includes all space between and in close proximity to the electrodes. The capacitor of the present invention includes the palladium islands as well as the dielectric substrate (and ambient atmosphere in close proximity to the capacitor). When the ambient atmosphere contains hydrogen, it diffuse into the palladium islands, changing their size and electrical properties, thereby changing the dielectric value of the dielectric region, and the impedance of the capacitor.

The inclusion of subelectrodes, particularly in an interdigitated fashion, reduces the volume of dielectric material in the dielectric region of the capacitor. This increases the sensitivity of the sensor to changes in the palladium islands case by the diffusion of hydrogen. By adjusting the degree of interdigitation, the interdigitated subelectrode distance, and the size of the capacitor, the concentration range of hydrogen sensitivity may be adjusted. Hydrogen concentration ranges (volume/volume) include 0.1 to 100%, 1.0 to 50%, including 2.0, 3.0, 4.0, 5.0, 6.0, 7.0, 8.0, 9.0, 10, 15, 20, 25, 30, 35, 40 and 45%.

The leads and the first and second electrodes may be formed of any electrically conductive substance, including metals (such as gold, silver, copper, aluminum and platinum, and alloys thereof), heavily doped semiconductors, organic conductors, graphite and graphene. The dielectric substrate may be made from any dielectric material, including oxides (such as ceramics, silicon oxide, silicon oxynitride, titanium oxide and aluminum oxide), nitrides (such as silicon nitride and aluminum nitride), and plastics; particularly useful would be silicon oxide on silicon. Preferably, the dielectric substrate has a surface roughness of 1 to 10 μm.

The area of the capacitor, which is the area between the first and second electrodes, is preferably 0.25 to 2500 mm$^2$ (0.5 mm×0.5 mm to 50 mm×50 mm), including 1.0, 4.0, 9.0, 16, 25, 36, 49, 64, 81, 100, 400, 900 and 1600 mm$^2$. The pitch of the subelectrodes is one hundredth to one half times the length of the first or second electrodes, including one fiftieth, one fortieth, one thirtieth, one twentieth, one tenth, one fifth, one fourth, and one third. Examples of the pitch include 0.05 to 100 mm, and 0.1 to 10 mm, such as 0.2, 0.25, 0.5, 1, 2, 3, 4, 5, 6, 7, 8 and 9 mm. Similarly, the width of the subelectrodes may be 0.05 to 100 mm, or 0.1 to 10 mm, such as 0.2, 0.25, 0.5, 1, 2, 3, 4, 5, 6, 7, 8 and 9 mm. Lastly, the number of subelectrodes, of either the first and/or the second electrodes, may be independently 1 to 100, or 2 to 50, including 3, 4, 5, 6, 7, 8, 9, 10, 12, 15, 20, 25, 30, 35, 40 or 45.

The palladium islands may have any thickness or size as long as they are in electrical isolation—that is, not in electrical contact with the leads nor first and second electrodes, nor in contact with each other. Preferably, the palladium islands are formed by forming a layer of palladium on the dielectric substrate which is too thin to form a continuous film, for example 1 to 8 nm thick, preferably 3 to 7 nm thick, including a 4, 5 or 6 nm thick film. Such films may be formed by a variety of techniques, including evaporation, sputtering and MOCVD. However, thicker and larger islands are possible, as long as at least 10 islands are present on the dielectric substrate of the capacitor. The palladium islands must be present in the dielectric region of the capacitor, between the first and second electrodes. Optionally, the palladium islands may contain other metals or elements, as long as hydrogen diffuses through the palladium islands substantially as does pure palladium.

The impedance of the capacitor is used to determine the concentration of hydrogen in the ambient atmosphere to which the sensor is exposed. Impedance is measured using an alternating current (AC) of at least 1 Hz, and preferably at least 1 kHz, including 1-100 kHz, such as 1, 2, 3, 4, 5, 6, 7, 8, 9 or 10 kHz. An LCR meter, many of which are commercially available, may be used to measure the inductance (L), capacitance (C), and resistance (R) of the capacitor, from which the impedance of the sensor may be calculated. Impedance may also be measured with an impedance meter or an RF filter circuit. An electrical device which includes the sensor and a device for measuring impedance is a complete system for measuring hydrogen concentrations.

EXAMPLES

All sensors were designed to have identical effective area of 4750 μm by 5000 μm and having pitches of 250 μm. The positive and negative electrodes have the same length and width of 4750 μm and 125 μm respectively. The sensors were fabricated on three different materials with different fabrication process. All sensors have equal numbers of electrodes (thirteen). The only parameter changing in the sensor design is the spacing between two adjacent positive and negative electrodes between which the electric field-lines exist. Sensor 1_11 was designed to have two positive electrodes at each end separated by eleven negative electrodes. Sensor 1_5 and Sensor 1_3 were designed with the same dimensions but with different configurations. Sensor 1_5 contains five negative electrodes between two positive electrodes and has the same pitch identical to Sensor 1_11. Sensor 1_3 contains three negative electrodes between two positive electrodes. Table 1 shows the parameters for novel interdigital sensors. FIG. 2 shows the representation of sensor configuration #1 (Sensor 1_11), where X=4.75 mm. Y=4.75 mm, and Z=0.25 mm. FIG. 1 depicts the sensor design. (The rectangular pads are the mounting are for a series resistor. In this experiment the chip resistor was replaced with a zero-ohm jumper.) The sensors were fabricated on alumina as a substrate used standard thick film printing methodology. The initial design was patterned on AUTOCAD® and then transferred on to a FIRE® 9500 photoplotter. The design was then transferred on to three different 325 mesh screens. The first trace layer was printed using PdAg 850° C. firing alloy. The second layer was made using a 850° C. silver material. The prepared paste was then dried at a 150° C. to ensure the right moisture content. Finally, the dried substrate was placed on a belt firing furnace profiled at 850° C.+5° C. for approximately ten minutes. The entire process for each layer was about thirty minutes long and was repeated for each layer. The last layer is a low thermal conductivity dielectric, which is used to control the solder flow, during the process of placing the chip resistor. For the low thermal conductivity dielectric, the "firing cycle" was modified to fire the low temp paste at 600° C. The ceramic is laser scribed so that the sensors can be separated by breaking by hand for evaluation.

TABLE 1

Interdigitated sensor dimensions

| Sensor | Sensor Area mm$^2$ | Pitch mm | # electrodes positive | negative |
|---|---|---|---|---|
| sensor 1_11 | 23.75 | 0.125 | 2 | 11 |
| sensor 1_5 | 23.75 | 0.125 | 3 | 10 |
| sensor 1_3 | 23.75 | 0.125 | 4 | 9 |

Figure 3:
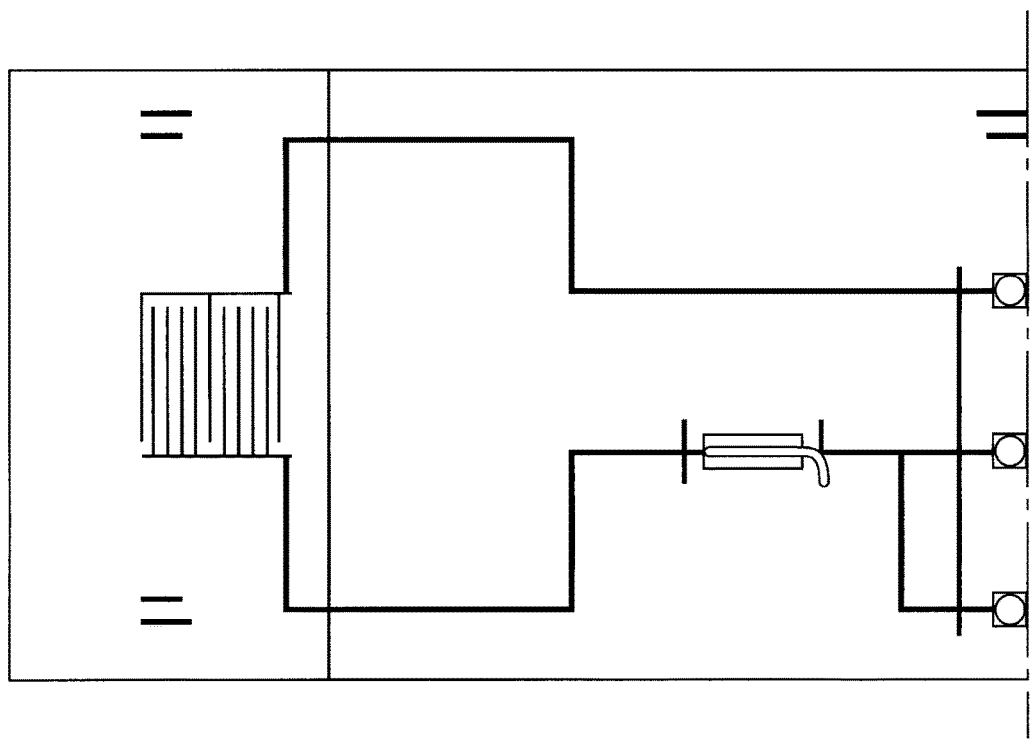
FIG. 3 is a photograph of a finished hydrogen sensor.

The sensors were then cleaned in de-ionized water and subsequently dried using atmospheric nitrogen. The printed substrates were then masked using aluminum foil with the interdigitated electrodes exposed and placed in a BJD-1800 TEMESCAL E-Beam system with an INFICON crystal deposition rate controller and the chamber was evacuated to $2\times10^{-6}$ Torr. The palladium was deposited to a target thickness of 5 nm. The alumina has an average surface roughness of 5 μm. Palladium tends to form islands of nano-sized crystallites when deposited around 5 nm of thickness and when combined with the roughness of the alumina isolate palladium structures are formed. FIG. 3 is a photograph of the finished hydrogen sensor using a wire jumper to short out the chip resistor pad. The five nanometers of thermal evaporated palladium is covering the sensor.

Preliminary modeling of the electric displacement field (D-field) indicates that it is confined to the surficial region when the palladium is deposited on the ceramic substrate. The simulation shows that the field is intensified in the interelectrode region thus enhancing the capacitive effects and hence the reactance of the sensor with AC excitation applied. The simulation was performed using both atmospheric nitrogen and oxygen and hydrogen test cases but does not account for the electrical response when molecular hydrogen is diffused into the palladium surficial layer, however.

The impedance of the sensing film was studied by employing an AGILENT 8480 LCR meter. The complete test station consisted of the AGILENT LCR meter, a cooling system (water bath) to maintain constant temperature, a computer with custom data logging software, gas cylinders, flow regulators, a one liter NALGENE® mixer tank, tubing and sensors. Several experiments were performed using the portable electrochemical interface and impedance analyzer instrument, the IVIUM COMPACTSTAT®. It reduces the noise and provides galvanic isolation. This instrument was connected to the sensor, which was enclosed in a 60 ml NALOGENE® bottle. The sensor was exposed to $N_2$ gas and $H_2$ at different pressures. The LCR meter/datalogging was performed using a custom Visual Basic software application. The inlet and outlet tubing to the sample allow the gas into the tube-containing sample. The valve controls the flow rate of the gases from the cylinder to the sample. The flow rate of the gas was adjusted and passed through the mixer. The air in the tube was displaced slowly depending on the diffusion rate of the gas. The frequency, amplitude and the time was set in the measurement system. The device under test (BUT) was maintained at a constant temperature throughout this process. The resistance and capacitance values for every second were recorded and plotted on a spreadsheet. In order to get a baseline for each sensor, it was pretreated with $H_2$ and $N_2$ at 100% (v/v). Then the optimal performance of each sensor is determined by sweeping it at 100 mV (p-p) sinusoidal wave at 100 Hz and 1 KHz. The response wave was monitored until the Cs and Rs values were stabilized back to base line.

The impedance of the samples is both dependent on the resistance and the capacitance because the impedance due to capacitance is very large which in turn makes the response of the sensor more dependent on the resistance of the sample. The impedance from the R-C model for the sensor is given by $$Z = -jX_a + (R_p - jX)/(R_p * jX) \quad (1)$$

(where $X_a$ is the reactance of air).

Since the capacitance due to alumina is very low (in pF), the reactance jX would be very large when compared to the resistance $R_p$. Therefore the value of $$Rp - jX = -jX \quad (2).$$

Then the R-C circuit model reduces to simple R-X model and the impedance (Z) is given by $$Z = R_p - jX_a \quad (3).$$

Therefore magnitude of Z is $$|Z| = \sqrt{(R_p)^2 + (X_a)} \quad (4)$$

and the phase angle is $\arctan(X_a/R_p)$ So the capacitance mainly affects the phase angle of the impedance.

The test structures were studied for the variation of resistance. Sample 1 was taken and placed in the glass tube, and the glass tube was immersed in water in a temperature controlled thermal bath maintained at 5° C. Hydrogen gas was passed through the tubing at a flow rate of 0.472 LPH (Liters Per Hour) air for 50 minutes. This allowed for a certain amount of pretreatment. The acquisition software was run after 20 minutes, allowing the gas to diffuse through the nanoparticles and the resistance, capacitance values were plotted on the desktop with the LCR meter. The frequency was set to 1 KHz. Next, the hydrogen gas was turned off and the nitrogen gas was passed at a flow rate of 0.944 LPH air for 50 minutes at 1 KHz and the resistance, and capacitance values were recorded.

Calculation of time required by the gases to displace inside the mixer, tubing and sensor chamber is as follows:
Volume of the glass tube=125 ml.
Volume of the mixer tank=1000 ml.
Total length of the tubing=188 cms.
Radius of the tube=0.2 cm.
Volume of the tubing is $\pi r^2 l$=23.634 ml.
Total volume to be displaced is 1148.634 ml.

Flow rate for hydrogen is 1.0 SCFH air, that is 28.317 liters per hour.

Hence, the lag time or displacement time=(volume to be displaced*60)/28.317=140 seconds and the flow rate of hydrogen is 140 seconds, and is the time taken for hydrogen to displace the air in the glass tube. The flow rate for nitrogen is 2.0 SCFH air, that is 2*28.317 liters per hour so that the time required by nitrogen to displace the air in the glass tube will be 70 seconds. In the experiment, the resistance and capacitance values were recorded 20 minutes after the sample was exposed to the gases. For hydrogen, the first 140 seconds would be taken to replace the air in the tube and the remaining time would be for diffusion of gases in to the platinum nanoparticles, and then 10 times the above time was given to completely displace the air. For nitrogen the first 70 seconds would be displacement time and the remaining time of the experiment was required for diffusion.

Results

Figure 4:
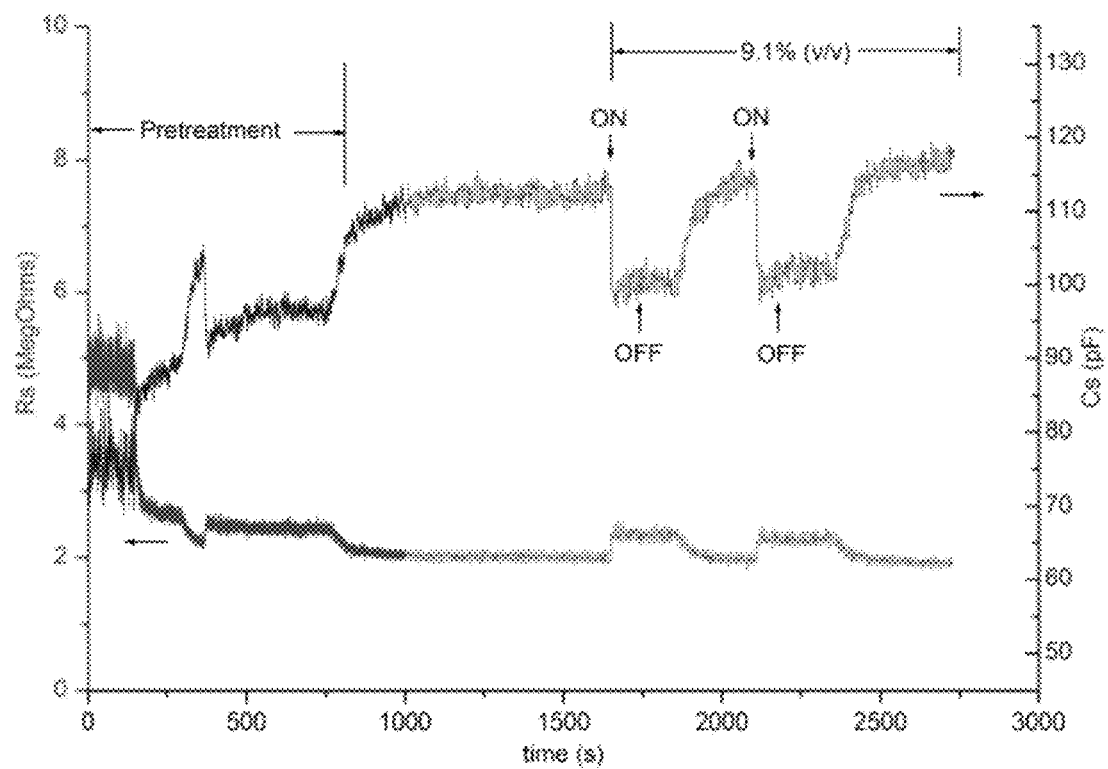
FIG. 4 is a graph of the behavior exhibited by sensors upon initial exposure to $H_2$ (first 1000 seconds) and during cycling of $H_2$. A change in resistance and capacitance was observed as the $H_2$ was cycled.
Figure 5:
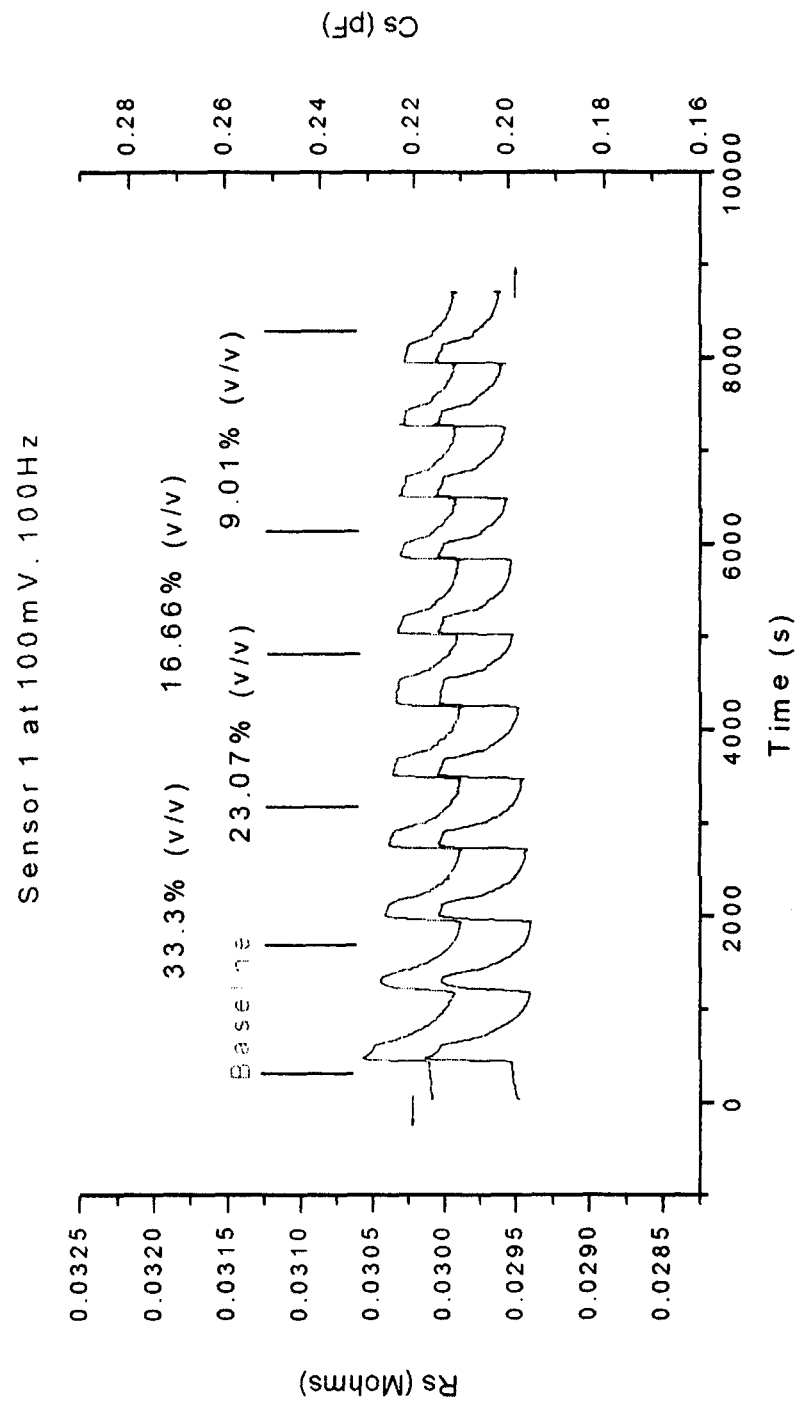
FIG. 5 is a graph of the resistive and reactive response shift for a sensor exposed to molecular hydrogen at five different concentrations (v/v) % at 100 mV and 100 Hz excitation. An identical response occurred with a 100 mV and 1 kHz excitation.
Figure 6:
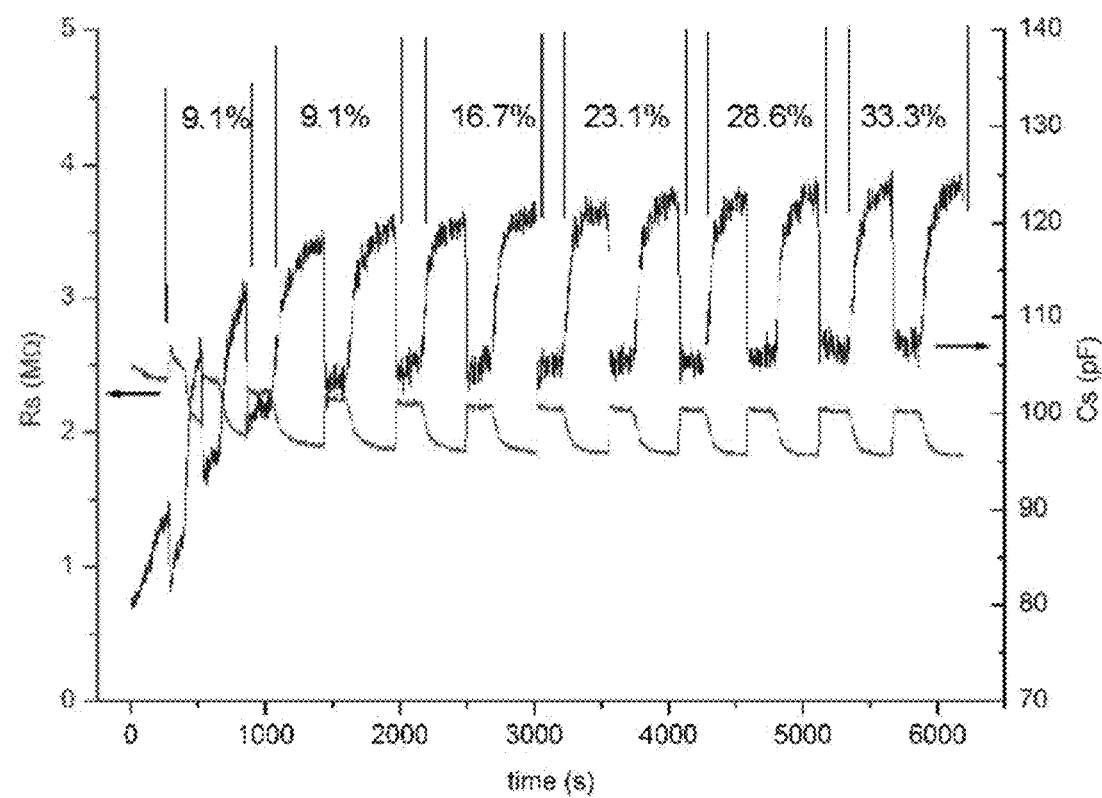
FIG. 6 is a graph of the response of a typical sensor indicating that a GO/NO GO condition occurs for concentrations greater than 9% $H_2$. The response appears to be geometry dependent.

The results of testing for a representative sensor of configuration 1, of the platinum embedded nanoporous alumina are shown in the FIGS. 4, 5 and 6. The raw data were normalized due to the non-Kelvin connected sensors. Kelvin connections allow for the neutralization of contact resistances and without that the impedance added will cause significant variation in the measurement. Four sensors were made with this film and all exhibited similar relative behavior. Experimentation determined that the sensor mounting method causes excessive variation of resistance. The samples were first exposed to air at room temperature and then exposed to nitrogen (carrier gas) and held at constant temperature with pretreatment using 100 mV 1 kHz sinusoidal excitation and 9.1% (v/v) molecular hydrogen. After an initial twenty-minute stabilization period, the real and imaginary parts of the impedance were recorded at one second intervals. After the pretreatment period (initial exposure to molecular hydrogen) the impedance increased and subsequently decreased as the hydrogen was cycled off (see FIG. 4).

The distance from air to pure nitrogen or hydrogen is the displacement of 21% oxygen. It should also be noted that the solubility of the gas diffused into the solid will increase with the increasing temperature. Until the first point measured at twenty minutes, both the temperature in the tube and the gas in the tube were being changed. The ratio of maximum oxygen shift in the film when exposed to pure oxygen versus the minimum oxygen content in the film when the film is exposed to nitrogen is approximately 3.7 times. The impedance shift measured was 3 times at 40° C. These results tend to suggest that the impedance shift is probably due to the absorption and desorption of oxygen in the film.

Experimentation on the palladium particles with volumetric ratios of hydrogen to nitrogen of 9.1%, 18.7% 23.1%, 28.8% and 33.3% (v/v) were performed on each of the three sensor configurations. Sensor 1 exhibited a linear shift in both the real and imaginary components (resistive and reactive or capacitance) with these volumetric ratios (FIG. 5). The first set of experiments was performed with a baseline measurement of 33.3% $H_2$ gas cycling and the concentrations were subsequently decreased. The initial excitation frequency was 100 Hz.

Subsequent experimentation with increased $H_2$ concentrations using sensors 2 and 3 indicated that the sensor could not discriminate among the various concentrations (FIG. 6). These sensors were exposed to the $N_2$ carrier gas and 9.1% $H_2$ and cycled with increasing concentrations of 16.7%, 23.1% and 33% (v/v). A typical capacitance increase of 12 pF was observed for all concentrations and nominal resistance decrease of 0.4 MO was observed.

CONCLUSION

The results of this experiment indicate that a nanoporous film containing palladium can detect the presence of molecular hydrogen. The overall response and ability to discriminate volumetric concentrations of molecular hydrogen exhibit a dependency on electrode geometry and placement.

REFERENCES

T. Xu, M. P. Zach, Z. L. Xiao, D. Rosenmann, U. Welp, W. K. Kwok and G. W. Crabtree, "Self-assembled monolayer-enhanced hydrogen sensing with ultrathin palladium films" *Appl. Phys. Lett,* 86, 203104 (2005).

Srinivasan, U., Houston, M. R., Howe, R. T., and Maboudian, R. "Alkyltrichlorosilane-based self-assembled monolayer films for stiction reduction in silicon micromachines" *Journal of Microelectromechanical Systems*, Vol. 7 Issue 2 Jun. 1998.

X. Q. Zeng, Y. L. Wang, Z. L. Xiao, M. L. Latimer, T. Xu and W. K. Kwok, "Hydrogen responses of ultrathin Pd films and nanowire networks with a Ti buffer layer" *Journal of Materials Science* 47, 6447 (2012).

Ali, M., et al, "Pt/GaN Schottky diodes for hydrogen gas sensors" *Sensors and Actuators B: Chemical,* 113, no. 2 (2006):797-804.

Frederic, Favier "Hydrogen Sensors and Switches from Electrodeposited Palladium Mesowire Arrays" *American Association for the Advancement of Science* 293, no. 5583 (2001): 2227-2231.

Neudeck, Philip G., David J. Spry, Andrew J. Trunek, Laura J. Evans, and Liang Y. Chen "Hydrogen Gas Sensors Fabricated on Atomically Flat 4HSiC Webbed Cantilevers" *Materials Science Forum* 600, no. 603 (2009):1199-1202.

Kocanda, Martin, Micheal Haji-Sheikh, and David S. Ballatine "Detection of Cyclic Volatile Organic Compounds Using Single-Step Anodized Nanoporous Alumina Sensors" *Sensors Journal, IEEE.* 9. no. 7 (2009): 836-841.

Kocanda, Martin "Enhanced hydrogen sensing employing electrodeposited palladium nanowires enclosed in anodized aluminum oxide nanopores" *Sensors,* 2009 IEEE Conference Publications, (2009): 308-311.

Syaifudin, A. R., S. C. Mukhapadhyay, P. L. Yu, Michael Haji-Sheikh, Chenghsin Chuang, John D. Vanderford, and Yao-Wei Huang "Measurements and Performance Evaluation of Novel Interdigital Sensors for Different Chemicals Related to Food Poisoning" *IEEE Sensors Journal,* vol. 11, no. 11, pp. 2957-2965, 2011.

A. R. Mohd Syaifudin, S. C. Mukhopadhyay and P. L. Yu "Modeling and Fabrication of Optimum Structure of Novel Interdigital Sensors for Food Inspection" Wiley: International Journal of Numerical Modeling: Electronic Networks, Devices and Fields. Vol. 24, Issue 6. Pp. 1-18. DOI: 10.1002/jnm.813. ISSN: 1099-1204. 1st Feb. 2011.

A. R. Mohd Syaifudin, K. P. Jayasundera and S. C. Mukhopadhyay "A Low Cost Novel Sensing System for Detection of Dangerous Marine Biotoxins in Seafood," *Elsevier—Sensors and Actuators B: Chemical. Volume* 137, Issue 1, 28 Mar. 2009, Pages 67-75. doi:10.1016/j.snb.2008.12.053.

What is claimed is:

1. A capacitor for a hydrogen sensor, comprising:
a dielectric substrate,
a first electrode, on the dielectric substrate,
a second electrode, on the dielectric substrate, and
palladium islands, on the dielectric substrate and between the first and second electrodes,
wherein the palladium islands are electrically isolated from the first and second electrodes and from each other,
the capacitor has an area of 0.25 to 2500 mm$^2$,
the dielectric substrate has a surface roughness of 1 to 10 µm,
the first electrode comprises first subelectrodes, and the second electrode comprises second subelectrodes,
the first subelectrodes and the second subelectrodes are interdigitated, and the interdigitated first and second subelectrodes have a pitch of 0.1 to 10 mm.

2. The capacitor of claim 1, having an area of 9.0 to 100 mm$^2$.

3. The capacitor of claim 1, wherein the number of first and second subelectrodes is 2 to 50.

4. The capacitor of claim 1, wherein the palladium islands have a thickness of 1 to 8 nm.

5. A hydrogen sensor, comprising
the capacitor for a hydrogen sensor of claim 1, and
electrical leads, on the substrate, electrically connected to the first and second electrodes.

6. The hydrogen sensor of claim 5, further comprising a plurality of capacitors for a hydrogen sensor.

7. The hydrogen sensor of claim 5, wherein the capacitor has an area of 9.0 to 100 mm$^2$.

8. The hydrogen sensor of claim 5, wherein the number of first and second subelectrodes is 2 to 50.

9. The hydrogen sensor of claim 5, wherein the palladium islands have a thickness of 1 to 8 nm.

10. A device for detecting hydrogen, comprising:
the hydrogen sensor of claim 5, and means for measuring impedance, electrically connected to the hydrogen sensor.

11. The device of claim 10, wherein the means for measuring impedance comprises an LCR meter, an impedance meter or an RF filter circuit.

12. The capacitor of claim 1, wherein the dielectric substrate is aluminum oxide and silicon oxide on silicon.

13. The capacitor of claim 1, wherein the dielectric substrate is silicon oxide on silicon.

14. The device of claim 10, wherein the number of first and second subelectrodes is 2 to 50, and the palladium islands have a thickness of 1 to 8 nm.

15. The hydrogen sensor of claim 5, wherein the dielectric substrate is aluminum oxide and silicon oxide on silicon.

16. The hydrogen sensor of claim 5, wherein the dielectric substrate is silicon oxide on silicon.

17. The device of claim 10, wherein the dielectric substrate is aluminum oxide and silicon oxide on silicon.

18. The device of claim 10, wherein the dielectric substrate is silicon oxide on silicon.

19. The capacitor of claim 1, wherein the number of first and second subelectrodes is 2 to 50, and the palladium islands have a thickness of 1 to 8 nm.

20. The hydrogen sensor of claim 5, wherein the number of first and second subelectrodes is 2 to 50, and the palladium islands have a thickness of 1 to 8 nm.

\* \* \* \* \*